United States Patent
Villa et al.

[19]

[11] Patent Number: 5,883,009
[45] Date of Patent: Mar. 16, 1999

[54] METHOD OF FABRICATING INTEGRATED SEMICONDUCTOR DEVICES COMPRISING A CHEMORESISTIVE GAS MICROSENSOR

[75] Inventors: Flavio Villa, Milan; Paolo Ferrari, Gallarate; Benedetto Vigna, Potenza, all of Italy

[73] Assignee: SGS-Thomson Microelectronics S.r.l., Agrate Brianza, Italy

[21] Appl. No.: 903,531

[22] Filed: Jul. 30, 1997

[30] Foreign Application Priority Data

Jul. 31, 1996 [EP] European Pat. Off. .............. 96830436

[51] Int. Cl.$^6$ .................................................. H01L 21/00
[52] U.S. Cl. ................ 438/739; 216/2; 216/33; 257/414; 438/49; 438/743; 438/756
[58] Field of Search .......................... 216/2, 33; 438/48, 438/49, 54, 735, 739, 743, 744, 756, 757; 257/414, 467

[56] References Cited

U.S. PATENT DOCUMENTS

| | | | |
|---|---|---|---|
| 4,580,439 | 4/1986 | Manaka | 73/23 |
| 5,242,863 | 9/1993 | Xiang-Zheng et al. | 437/228 |
| 5,510,276 | 4/1996 | Diem et al. | 438/739 X |
| 5,618,345 | 4/1997 | Saitoh et al. | 216/2 |
| 5,622,633 | 4/1997 | Ohtsuke et al. | 438/739 X |
| 5,801,070 | 9/1998 | Zanini-Fisher et al. | 216/2 |

FOREIGN PATENT DOCUMENTS

| | | |
|---|---|---|
| 0 346 127 | 12/1989 | European Pat. Off. . |
| WO 95/10770 | 4/1995 | WIPO . |

OTHER PUBLICATIONS

European Search Report from European Patent Application 96830436.0, filed Jul. 31, 1996.

*A Microfabricated Floating–Element Shear Stress Sensor Using Wafer–Bonding Technology,* Shajii et al, J of Microelectromechanical Sys, vol. 1, Jun. 1992, pp. 89–94.

*Basic Micro Module For Chemical Sensors With On Chip Heater And Buried Sensor Structure;* Mutschall et al, The 8th Intnl Conf on Solid–State Sensors and Actuatorsand Eurosensors, pp. 256–259.

*Micromachining and ASIC Technology,* Stoffel, Microelectronics J, 25 (1994) pp. 146–156.

*Advanced Bulk Micromachining of Silicon for Thermal Insulation of Sensors,* Amato et al., Sensori per Avanzate––Brescia, 1996, pp. 49–50.

*Sensor Technology Motorola's Portfolio,* Motorola Sensors–8, Presentazione, Mororola in Ford.

*A High Sensitivity CMOS Gas Flow Sensor Based On An N–Poly Thermopile,* Moser et al., OSC–vol. 40.

*A Microfabricated Floating–Element Shear Stress Sensor Using Wafer–Bonding Technology,* Shajii et al., J electromechanical Sys., vol. 1, No. 2, Jun. 1992.

*Theory of Plates and Shells,* Timoshenko et al., Engineering Societies Monographs, Second Edition.

*Primary Examiner*—William Powell
*Attorney, Agent, or Firm*—Wolf, Greenfield & Sacks, P.C.

[57] ABSTRACT

The chemoresistive gas sensor comprises a heating element integrated in a dedicated SOI substrate having an air gap in the intermediate oxide layer between two wafers of monocrystalline silicon. A sensitive element of tin oxide is formed over the heating element and separated from it by a dielectric insulating and protective layer. A trench formed at the end of the fabrication of the device, extends from the surface of the wafer in which the heating element is integrated, up to the air gap to mechanically separate and insulate the sensitive element from the rest of the chip, thereby improving the mechanical characteristics sensitivity and response of the sensor.

41 Claims, 3 Drawing Sheets

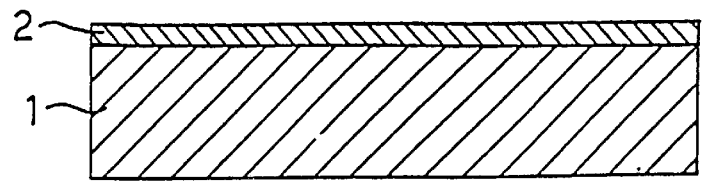
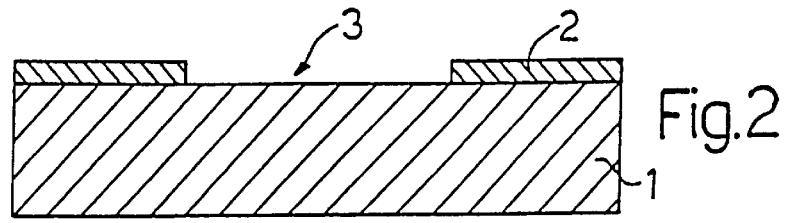
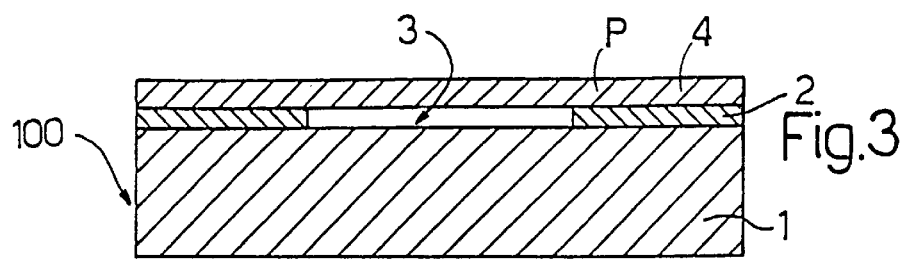
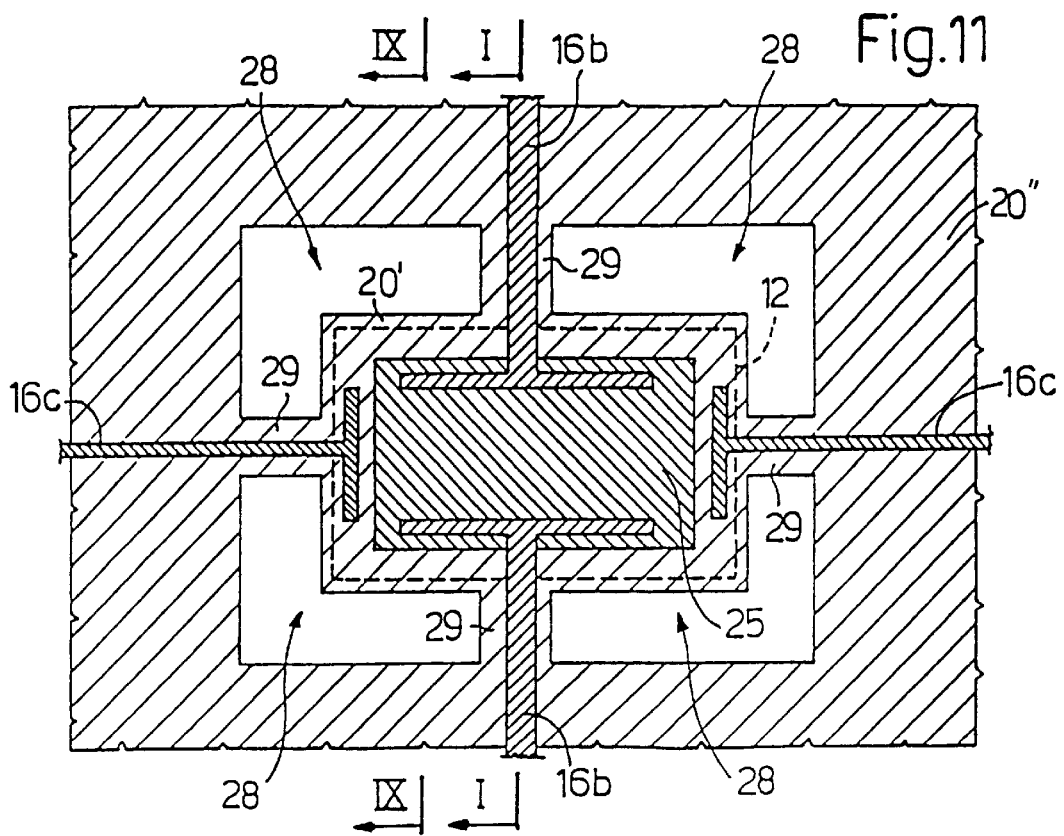

METHOD OF FABRICATING INTEGRATED SEMICONDUCTOR DEVICES COMPRISING A CHEMORESISTIVE GAS MICROSENSOR

BACKGROUND OF THE INVENTION

1. Field of the Invention

The present invention relates to a method of fabricating integrated semiconductor devices comprising a chemoresistive gas microsensor.

2. Discussion of the Related Art

As is known in the art, chemical sensors detect the presence of a gas by virtue of a chemical reaction between the molecules of a gas and a sensitive film. The chemical reaction depends to a large extent on operating temperature, which affects the adsorption, desorption and diffusion of the gas in the film. Therefore operating temperature is an important factor in optimizing the performance of the sensor, particularly in terms of sensitivity, selectivity and response time. Thus, sensors are equipped with temperature regulating and control means that allow optimization of operation.

In recent times, integrated chemoresistive gas microsensors have been fabricated using microelectronics technology. Such sensors present numerous advantages: low fabrication cost; low in-service energy consumption; rapid response time; and integration with the temperature control and output signal processing circuit.

Integrated gas microsensors which are now being marketed feature chemoresistive tin oxide diaphragms deposited on a wafer of bulk-micromachined semiconductor material, and detect the presence of gas as a change in the resistance of the film caused by a chemical reaction, on the surface of the diaphragms between the oxygen of the diaphragm and the gas.

To function properly, the sensors must be maintained at a temperature of about 400° C. Therefore, they are provided with heating elements, and must be thermally isolated from the rest of the chip integrating the signal control and processing circuit.

Various techniques are known for isolating the sensitive portion from the rest of the chip. The traditional technique is bulk micromachining, which consists of forming the sensitive portion on or in a dielectric layer deposited on a massive silicon wafer, and in removing a portion of the silicon from the rear of the wafer by plasma or wet etching. The dielectric layer performs the dual function of mechanically supporting the sensor and thermally isolating it from the silicon wafer. Using this technique, prototypes have been formed wherein part of the silicon is removed from the sensor area and only part of the thickness of the wafer is etched, whereas in other prototypes, all the silicon is removed at the sensor area (etching extending up to the dielectric layer supporting the sensor element). Details of the latter solution are to be found, for example, in the article entitled "Basic micro-module for chemical sensors with on-chip heater and buried sensor structure" by D. Mutschall, C. Scheibe and E. Obermeier.

Bulk micromachining, however, requires front-rear processing and such particular handling of the wafers as to be incompatible with current integrated circuit fabrication methods.

Another technique is front micromachining, whereby the massive silicon wafer or a sacrificial layer is etched from the front, and a dielectric layer mechanically supports and thermally isolates the sensor element. Details of this technique, relative to the fabrication of a different type of sensor, are to be found in the article entitled "A high-sensitivity CMOS gas flow sensor based on an N-poly/P-poly thermopile" by D. Moser and H. Baltes, DSC-Vol 40, Micromechanical Systems, ASME, 1992. A general review of bulk and front micromachining technology is found in the article entitled "Micromachining and ASIC technology" by Axel M. Stoffel, Microelectronics Journal, 25 (1994), p. 145–156.

Forming suspended structures using this technique, however, involves etching steps which are incompatible with current microelectronics fabrication processes, so that the sensors and relative control and processing circuits cannot be formed on one chip.

For sensors of a different type, dedicated SOI (Silicon-on-Insulator) substrates have been proposed, wherein the starting wafer comprises a Silicon-Silicon Oxide-Silicon stack with the oxide selectively removed at the sensor area to form an air gap. The trenches formed in the front of the wafer after contacting the air gap provide thermal isolation for the sensor. Details of this technique, relative to a shear stress sensor, are to be found, for example, in the article entitled "A Microfabricated Floating-Element Shear Stress Sensor Using Wafer-Bonding Technology" by J. Sliajii, Kay-Yip Ng and M. A. Schmidt, Journal of Microelectromechianical Systems, Vol. 1, N. 2, Jun. 1992, p. 89–94. The bonding technique used (excluding formation of the air gap) is also described in the article entitled "Silicon-on-Insulator Wafer Bonding-Wafer Thinning Technological Evaluations" by J. Hausman, G. A. Spierings, U. K. P. Bierman and J. A. Pals, Japanese Journal of Applied Physics, Vol. 28, N. 8, Aug. 1989, p. 1426–1443.

SUMMARY OF THE INVENTION

It is an object of the present invention to provide a fabrication method and chemoresistive gas sensor designed to overcome the drawbacks typically associated with known technology.

The present invention provides, in one embodiment, a method of fabricating integrated semiconductor devices that include chemoresistive gas microsensors comprising forming an SOI substrate of semiconductor material, forming a heating element in the SOI substrate, and forming a gas sensitive element upon the SOI substrate. The SOI substrate is formed by first forming an insulating material layer on a first semiconductor material wafer, followed by selectively removing a portion of the insulating material layer and then bonding a second wafer of semiconductor material to the insulating material layer to define an air gap. The air gap is defined by the first wafer, the second wafer and the insulating material layer.

After the gas sensitive element is formed, portions of the second wafer are selectively removed to form a trench that extends from a surface of a second wafer to the air gap. The trench includes a number of trench portions that extend in a closed line along the periphery of the air gap. The trench portions are separated by connecting and supporting arms formed by the second wafer.

The heating element is formed by implanting the SOI substrate with a doping agent in a portion over the air gap; conductivity regions of integrated electronic components may also be implanted simultaneously.

The gas sensitive element is formed by forming a protective layer of insulating material on the SOI substrate and forming a sensitive region of gas sensitive material over the protective layer. After the protective layer is formed, contact portions are opened in the protective layer, a metal material is deposited over the protective layer and subsequently defined to form contact areas. Forming the sensitive region also includes the steps of depositing and defining a layer of gas sensitive material over the heating element. The metal material used for the contacts can be either titanium, platinum and chromium or alternatively tungsten. Preferably the gas sensitive material used in the sensitive region is tin oxide and may further include a catalyst which is preferably platinum and palladium.

The present invention also provides an integrated semiconductor device comprising a semiconductor material substrate which is preferably an SOI substrate and a chemoresistive gas microsensor that includes a heating element and gas sensitive element. The SOI substrate includes two monocrystalline semiconductor material wafers separated by an insulating material layer having air gaps defined therein by the first wafer, the second wafer and the insulating material.

In one aspect of the present device, a trench extends from a surface of the second wafer to the air gap, and the trench includes a number of portions that extend in a closed line along a periphery of the air gap separated by connecting and supporting arms formed by the second wafer.

The heating element of the present integrated semiconductor device includes a region that is implanted with a doping agent in a portion of the second wafer over the air gap. The implanted region is overlaid with a protective region of insulating material and a sensitive region of gas sensitive material. Preferably the gas sensitive material is tin oxide overlaid with platinum and palladium. The contact regions of metal material are connected electrically to the implanted and sensitive regions and also to the conductivity regions of an integrated electronic component. The metal material used for the contact areas includes titanium, chromium and platinum or alternatively tungsten.

The chemoresistive gas sensor of the present integrated semiconductor device is designed to detect a change in a resistance of the gas sensitive material included in the gas sensitive element. The gas sensitive material contains oxygen, the molecules of which react in the presence of a gas to produce a change in a resistance of the gas sensitive material. The chemoresistive gas microsensor preferably operates at an elevated temperature, which is produced when the heating element heats the gas sensitive element.

The foregoing and other objects, features, aspects and advantages of the invention will become apparent from the following detailed description of the present invention when taken in conjunction with the accompanying drawings.

BRIEF DESCRIPTION OF THE DRAWINGS

In the drawings:

FIGS. 1 to 8 show cross sections of a semiconductor material wafer at successive steps in the fabrication method according to the present invention;

FIG. 11 shows a larger-scale top plan view of a portion of the FIG. 10 wafer.

DETAILED DESCRIPTION

Figure 4:
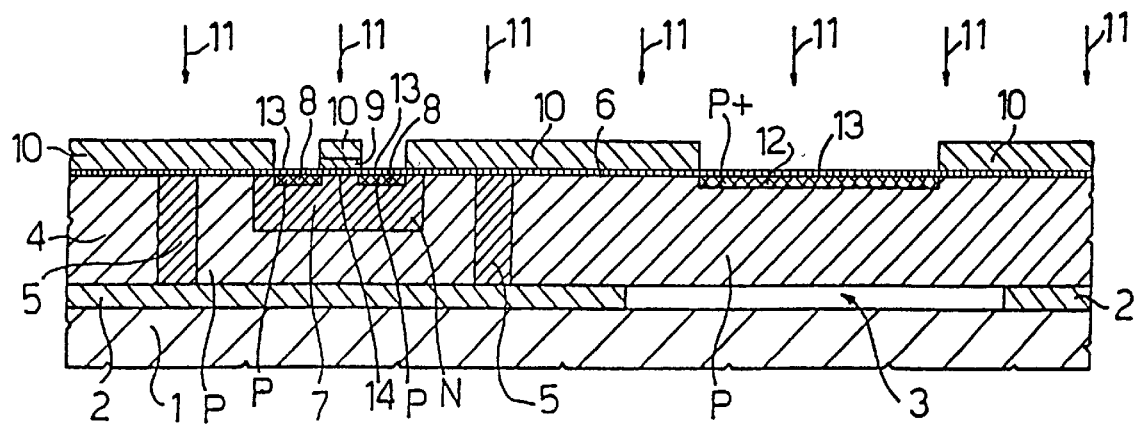

In the present fabrication method, a silicon oxide layer 2 is formed, e.g. grown thermally, on a first wafer 1 of monocrystalline silicon (FIG. 1); oxide layer 2 is masked and etched to selectively remove a portion thereof and form an opening 3 to later form an "air gap" (FIG. 2); and a second wafer 4 of monocrystalline silicon, P-type in the example shown, is bonded to oxide layer 2 using, for example, the method described in the above article by J. Hausman, G. A. Spierings, U. K. P. Bierman and J. A. Pals, to form a dedicated SOI substrate 100 in which the air gap 3 is defined at the top and bottom by second and first wafers 4 and 1, and laterally by oxide layer 2.

At this point. SOI substrate 100 is processed as usual for forming integrated circuit bipolar and MOS electronic components. More specifically (FIG. 4), in second wafer 4, there are formed junction or dielectric insulating regions 5 extending from upper surface 6 of second wafer 4 to oxide layer 2, a PMOS transistor formed in an N-well 7 including P-type source and drain regions 8, and a control gate region 9 insulated from second wafer 4 by a gate oxide region 14. FIG. 4 also shows (schematically by arrows 11) self-aligned implanting, through a protective oxide layer 13 covering surface 6 of second wafer 4, of heater region 12 and source and drain regions 8 using a resist mask 10. Region 12 forms the heater of the gas sensor, as shown in FIG. 4.

Figure 5:
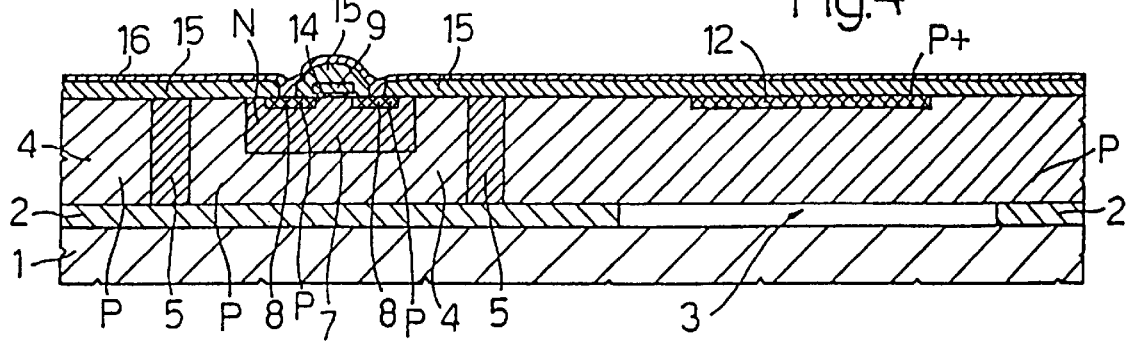

A dielectric protective layer 15 (e.g. of silicon nitride or BPSG-Boron Phosphorous Silicon Glass) is then deposited, which also provides electrical insulation of the heater from the sensitive element; the contacts are then opened and a metal layer 16 is deposited to form the contact electrodes (FIG. 5). Metal layer 16 may comprise a triple titanium-platinum-chromium layer or a single tungsten layer to permit higher operating temperatures of the finished device than with a conventional aluminum layer.

Figure 6:
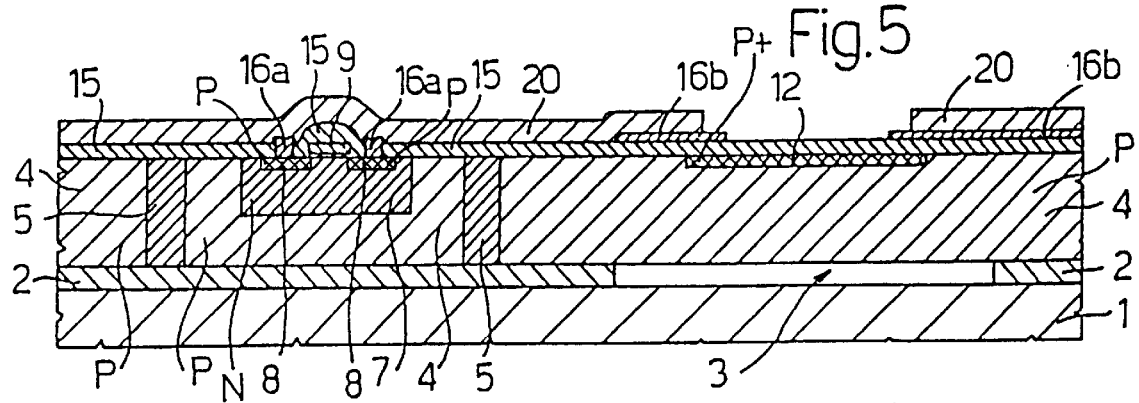

Metal layer 16 is then defined to form, on second wafer 4, metal contact region 16a for electronic component regions 8 and 9, region 16b for the sensitive element, and region 16c (shown only in FIG. 11) for the heater (region 12). A dielectric (e.g. TEOS-tetraethylorthosilicate) masking layer 20 is deposited and removed at the region in which the sensitive element is to be formed to obtain the intermediate structure shown in FIG. 6.

Figure 7:
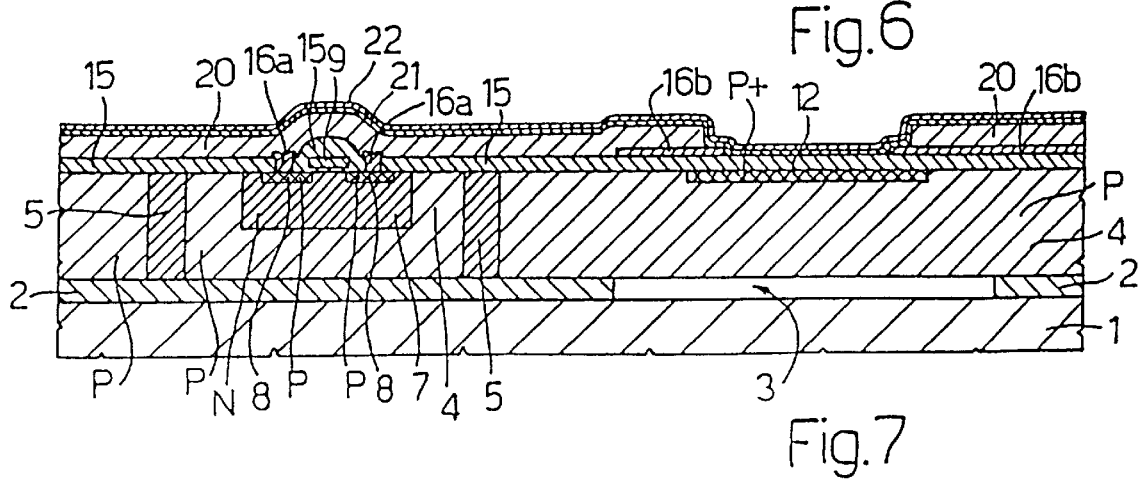

At this point, a tin oxide film 21 is deposited (e.g. by sputtering) and, over this, a platinum-palladium catalyst layer 22 which reduces the activation energy of the sensitive film 21 and assists the chemical reaction between the gas molecules and tin oxide (FIG. 7).

Figure 8:
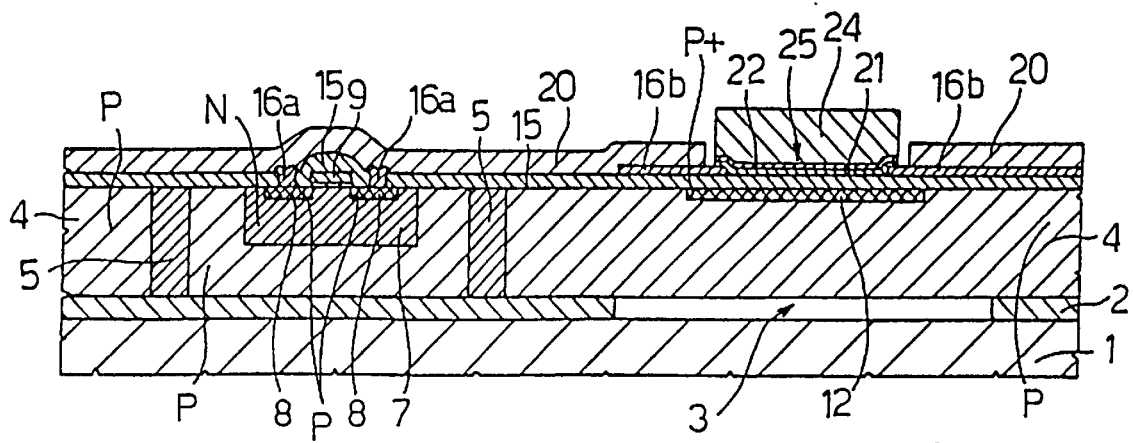
Figure 9:
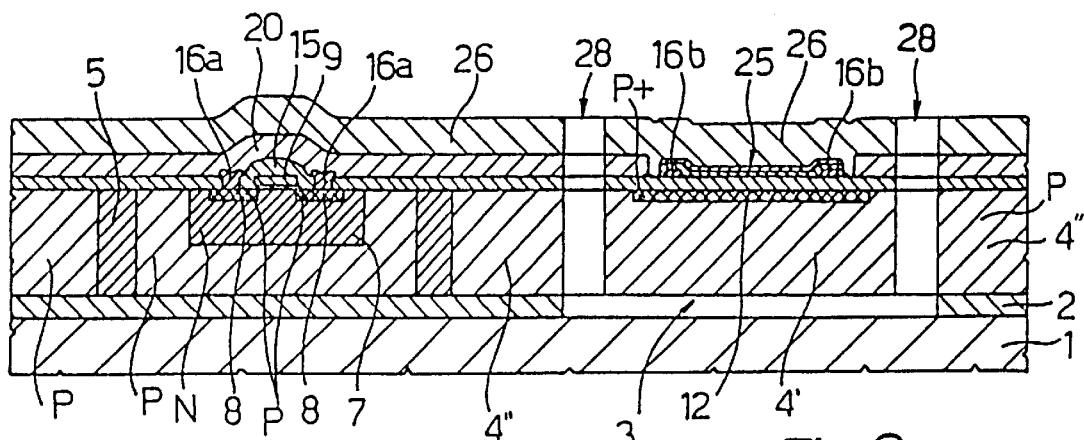
FIGS. 9 and 10 show cross sections in a different plane from that of FIGS. 1–8, at successive steps in the fabrication method according to the invention.
Figure 10:
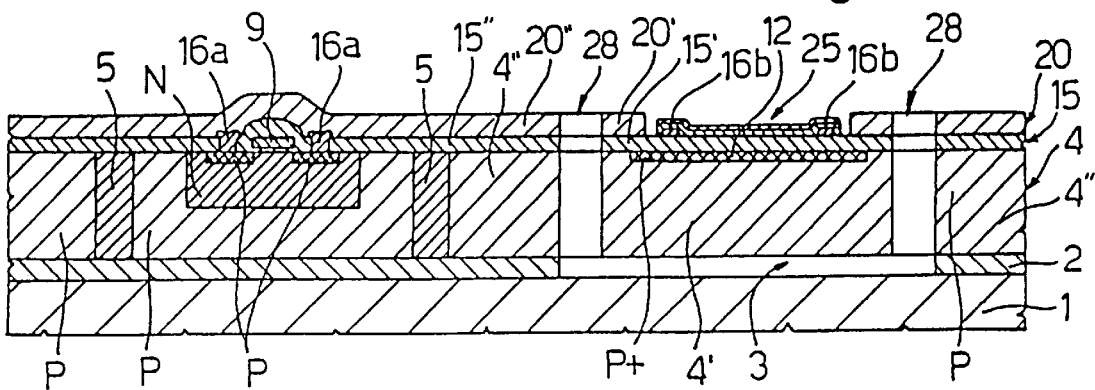

By photolithographic masking 24, tin oxide film 21 and catalyst layer 22 are defined to obtain the intermediate structure shown in FIG. 8, in which the remaining portions of film 21 and layer 22 form the sensitive element 25. After removal of mask 24, another resist mask 26 is deposited to facilitate excavation of a trench 28 which surrounds all sides (except connection portions) of the region of second wafer 4 supporting sensitive element 25 (see FIG. 8, which, in the sensor region, shows a different section from that in FIGS. 1–7). Using mask 26, portions of dielectric masking layer 20, of dielectric protective layer 15, and of second wafer 4 up to air gap 3 are removed, thereby forming trench 28, as shown in FIG. 9. Trench 28 preferably extends along a closed line, e.g. the sides of a rectangle (as shown in FIG. 11, in which dielectric protective layer 20 is removed) or along the circumference of a circle, so as to laterally define an inner portion 4' of second wafer 4, and advantageously extends along the periphery of air gap 3. Trench 28 comprises a number of portions separated by connecting and supporting arms 29 extending between inner portions 4', 15', 20' and respective outer portions 4", 15", 20" of wafer 4 and dielectric layers 15, 20 (FIG. 9) so that inner portion 4' is thermally isolated from the rest of the chip. Mask 26 is then removed to obtain the final structure shown in cross section in FIG. 10 and from above in FIG. 11.

The advantages of the fabrication method and sensor according to the present invention are as follows.

Using a SOI substrate 100, the method described is fully compatible with planar microelectronics technology, thus enabling the same advantages in terms of reliability, reproducibility and cost, as well as enabling the sensor and relative signal control and processing circuits to be integrated on one chip.

Moreover, as compared with known solutions involving anisotropic etching from the front or rear of the substrate, spatial integration of the sensor is improved, so that the sensor is smaller and requires less energy for it to operate compared with known sensors.

Forming the heater of monocrystalline silicon, instead of polysilicon, provides for a more uniform and faster heating of the sensor element 25. Indeed, the more uniform heating causes an improved selectivity and sensitivity of the sensor, while the faster heating reduces the response time of the sensor, giving rise to an improved operation thereof. And finally, the mechanical stability of the sensor is improved (Young and Poisson moduli less dependent on process parameters as compared with deposited films).

Clearly, changes may be made to the fabrication method and sensor as described and illustrated herein without, however, departing from the scope of the present invention. More specifically, the isolating regions in the second wafer may be of a different type, e.g. dielectric type instead of junction type; the electronic components integrated in the same chip may be both bipolar and MOS; the conductivity types of the various regions may be other than as shown; and the catalyst layer may be omitted.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting. The invention is limited only as defined in the following claims and the equivalents thereto.

What is claimed is:

1. A method of fabricating integrated semiconductor devices including chemoresistive gas microsensors, comprising the steps of:

forming a SOI substrate of semiconductor material;
   forming a heating element in said SOI substrate; and
   forming a gas-sensitive element on said SOI substrate.

2. A method as claimed in claim 1, wherein the step of forming a SOI substrate comprises the steps of:

forming an insulating material layer on a first wafer of monocrystalline semiconductor material;
   selectively removing a portion of said insulating material layer; and
   bonding a second wafer of monocrystalline semiconductor material to said insulating material layer, wherein said air gap is defined by said first wafer, said second wafer, and said insulating material layer.

3. A method as claimed in claim 2, wherein the step of forming a gas-sensitive element is followed by the step of selectively removing portions of said second wafer to form a trench extending from a surface of said second wafer to said air gap.

4. A method as claimed in claim 3, wherein said trench comprises a number of trench portions extending substantially in a closed line along the periphery of said air gap and said trench portions are mutually separated by connecting and supporting arms formed by said second wafer.

5. A method as claimed in claim 4, wherein the step of forming a heating element comprises the step of implanting said SOI substrate with a doping agent in a portion over said air gap.

6. A method as claimed in claim 4, wherein the step of forming a heating element comprises the step of implanting said second wafer in a portion over said air gap; and wherein the step of forming a gas-sensitive element comprises the steps of forming a protective region of insulating material over said second wafer, and forming a sensitive region of gas-sensitive material over said protective region.

7. A method as claimed in claim 5, wherein the step of implanting said SOI substrate is performed simultaneously with a step of implanting a conductivity region of an integrated electronic component.

8. A method as claimed in claim 7, wherein the step of forming a gas-sensitive element comprises the steps of:

forming a protective layer of insulating material on said SOI substrate; and
   forming a sensitive region of gas-sensitive material over said protective layer.

9. A method as claimed in claim 8, wherein said gas sensitive material comprises tin oxide.

10. A method as claimed in claim 9, wherein said gas sensitive material further comprises a catalyst.

11. A method as claimed in claim 10, wherein said catalyst comprises platinum and palladium.

12. A method as claimed in claim 8, wherein the step of forming a protective layer on said SOI substrate is followed by the steps of:

opening contact portions in said protective layer;
   depositing a metal material layer over said protective layer;
   defining said metal material layer; and
   wherein the step of forming a sensitive region further comprises the steps of:
      forming a masking structure including a window over said heating element;
      depositing a layer of said gas-sensitive material; and
      defining said layer of gas-sensitive material.

13. A method as claimed in claim 12, wherein the step of depositing a metal material layer further comprises the step of depositing titanium, platinum and chromium.

14. A method as claimed in claim 12, wherein the step of depositing a metal material layer further comprises the step of depositing a layer of tungsten.

15. An integrated semiconductor device comprising:

a semiconductor material substrate;
   a chemoresistive gas microsensor including a heating element and a gas-sensitive element, wherein said semiconductor material substrate is a SOI substrate, and said heating element is integrated in said SOI substrate.

16. A device as claimed in claim 15, wherein the SOI substrate comprises:

a first wafer of monocrystalline semiconductor material;
   an insulating material layer over said first wafer;
   a second wafer of monocrystalline semiconductor material over said insulating material layer, wherein said insulating material layer is interrupted at an air gap defined by said first and second wafers and by said insulating material layer.

17. A device as claimed in claim 16, further comprising a trench extending from a surface of said second wafer to said air gap.

18. A device as claimed in claim 15, wherein the trench comprises a number of trench portions extending substantially in a closed line along the periphery of said air gap, and wherein said trench portions are mutually separated by connecting and supporting arms formed by said second wafer.

19. A device as claimed in claim 17, wherein the heating element comprises a region implanted with a doping agent in a portion of said second wafer over said air gap.

20. A device as claimed in claim 18, wherein the heating element comprises a region implanted with a doping agent in a portion of said second wafer over said air gap.

21. A device as claimed in claim 19, further comprising a protective region of insulating material extending over a surface of said second wafer over said implanted region, and a sensitive region of gas-sensitive material extending over part of said protective region.

22. A device as claimed in claim 20, further comprising a protective region of insulating material extending over a surface of said second wafer over said implanted region, and a sensitive region of gas-sensitive material extending over part of said protective region.

23. A device as claimed in claim 21, wherein said gas-sensitive material comprises tin oxide overlaid with platinum-palladium.

24. A device as claimed in claim 22, wherein said gas-sensitive material comprises tin oxide overlaid with platinum-palladium.

25. A device as claimed in claim 21, further comprising contact regions of metal material connected electrically to said implanted and sensitive regions and to conductivity regions of an integrated electronic component.

26. A device as claimed in claim 22, further comprising contact regions of metal material connected electrically to said implanted and sensitive regions and to conductivity regions of an integrated electronic component.

27. A device as claimed in claim 25, wherein said metal material comprises a triple layer of titanium, chromium and platinum.

28. A device as claimed in claim 25, wherein said metal material comprises a layer of tungsten.

29. A device as claimed in claim 26, wherein said metal material comprises a layer of tungsten.

30. A device as claimed in claim 26, wherein said metal material comprises a triple layer of titanium, chromium and platinum.

31. The semiconductor device of claim 21, wherein said chemoresistive gas microsensor is a means for detecting a change in a resistance of said gas-sensitive material and the molecules of a gas.

32. The semiconductor device of claim 22, wherein said chemoresistive gas microsensor is a means for detecting a change in a resistance of said gas-sensitive material and the molecules of a gas.

33. The semiconductor device of claim 31, wherein said gas-sensitive material comprises oxygen.

34. The semiconductor device of claim 32, wherein said gas-sensitive material comprises oxygen.

35. The semiconductor device of claim 33, wherein said resistance change in said gas-sensitive material is produced when the molecules of a gas chemically react with said oxygen in said gas-sensitive material.

36. The semiconductor device of claim 32, wherein said resistance change in said gas-sensitive material is produced when the molecules of a gas chemically react with said oxygen in said gas-sensitive material.

37. The semiconductor device of claim 35, wherein said resistance change is detected by said gas microsensor at an elevated temperature.

38. The semiconductor device of claim 36, wherein said resistance change is detected by said gas microsensor at an elevated temperature.

39. The semiconductor device of claim 37, wherein said heating element heats said gas-sensitive element to produce said elevated temperature.

40. The semiconductor device of claim 38, wherein said heating element heats said gas-sensitive element to produce said elevated temperature.

41. The semiconductor device of claim 15, wherein said chemoresistive gas microsensor comprises an oxygen containing gas-sensitive material and said heating element heats said gas-sensitive material to an elevated temperature, such that said oxygen reacts with a gas at said elevated temperature to produce a resistance change in said gas-sensitive material.

* * * * *